(12) United States Patent
Yoo (10) Patent No.: US 10,796,598 B2
(45) Date of Patent: Oct. 6, 2020

(54) DEVICE AND METHODS FOR FORMING NEW SLEEPING FUNCTION AGAINST INSOMNIA

(71) Applicant: Keun-Young Yoo, Seoul (KR)

(72) Inventor: Keun-Young Yoo, Seoul (KR)

(\*) Notice: Subject to any disclaimer, the term of this patent is extended or adjusted under 35 U.S.C. 154(b) by 0 days.

(21) Appl. No.: 16/658,940

(22) Filed: Oct. 21, 2019

(65) Prior Publication Data
US 2020/0135047 A1   Apr. 30, 2020

(30) Foreign Application Priority Data
Oct. 31, 2018   (KR) .................. 10-2018-0132277

(51) Int. Cl.
| | | |
|---|---|---|
| *G09B 19/00* | (2006.01) | |
| *A61M 21/02* | (2006.01) | |
| *G06F 3/0484* | (2013.01) | |
| *G09B 5/06* | (2006.01) | |
| *G06F 3/0482* | (2013.01) | |
| *G06F 3/0483* | (2013.01) | |
| *G06F 3/16* | (2006.01) | |

(52) U.S. Cl.
CPC ............ *G09B 19/00* (2013.01); *A61M 21/02* (2013.01); *G06F 3/0482* (2013.01); *G06F 3/0483* (2013.01); *G06F 3/04847* (2013.01); *G06F 3/165* (2013.01); *G09B 5/06* (2013.01)

(58) Field of Classification Search
None
See application file for complete search history.

(56) References Cited

U.S. PATENT DOCUMENTS

| | | | | |
|---|---|---|---|---|
| 10,332,315 B2 * | 6/2019 | Samec | ............... | G02B 27/0172 |
| 2010/0323335 A1 * | 12/2010 | Lee | ........................ | A61M 21/00 434/236 |
| 2013/0245485 A1 * | 9/2013 | Mashour | .................. | A61B 5/74 600/544 |
| 2014/0024883 A1 * | 1/2014 | Rosenzweig | ......... | A61M 21/00 600/27 |
| 2017/0365101 A1 * | 12/2017 | Samec | ............... | G02B 27/0172 |

FOREIGN PATENT DOCUMENTS

KR    200254344    11/2001

\* cited by examiner

*Primary Examiner* — Jerry-Daryl Fletcher
*Assistant Examiner* — Daniel E Lane
(74) *Attorney, Agent, or Firm* — IPLA P.A.; James E. Bame (57) ABSTRACT

Provided is a functional learning/training device and methods for forming a sleeping function, which is distinct and independent of general sleeping function, and which enables the user to fall asleep quickly by overcoming the phenomenon of insomnia. When a new sleeping condition is set by actively generating visual activity every night, the phenomenon of insomnia may be solved, such that the user can fall sleep quickly and further, ultimately, with the use of the newly formed sleeping function, even without the use of the present invention, the user can solve the phenomenon of insomnia easily and fall asleep, as if a normal person sleeps in a general sleeping function under general circumstances.

1 Claim, 10 Drawing Sheets

DEVICE AND METHODS FOR FORMING NEW SLEEPING FUNCTION AGAINST INSOMNIA

CROSS REFERENCE

This application claims foreign priority under Paris Convention to Korean Patent Application No. 10-2018-0132277, filed 31 Oct. 2018, with the Korean Intellectual Property Office, which is incorporated herein with its entirety.

BACKGROUND

The present invention relates to a device and methods for performing brain functional training/learning which forms a new sleeping function against insomnia. In more detail, the present invention relates to a device and methods for brain functional training/learning to form a new(second) sleeping function which is completely different from a general sleeping function to overcome insomnia.

It is painful thing for a person to be unable to sleep all night. If a person cannot sleep at night, he or she will be hampered in daytime social activities, and his or her overall quality of life may be lowered.

Therefore, conventionally, sleeping pills have mainly been used to solve this phenomenon. However, if sleeping pills are used for an extended period of time, the user thereof may become resistant to such drugs and may not be able to fall asleep even after taking sleeping pills. In addition, taking sleeping pills(chemicals) is frequently accompanied by side effects. Thus, the use of sleeping pills as a fundamental solution to insomnia may be problematic.

On the other hand, when it comes to cognition, there is a well-known or commonly used art to induce sleep by listening to songs, music or sound. This is an attempt to solve the phenomenon of being unable to sleep by using auditory activity.

Korean Utility Model Application No. 20-2000-0007191 (Mar. 14, 2000) is an attempt to solve the phenomenon of being unable to sleep by putting herbal medicine in a pillow to produce an odor, which causes olfactory activity.

There is an attempt, as in Korean Utility Model Application No. 20-2001-0005507 (Mar. 2, 2001), to inject light into the eye pad to make the eyes tired and fall asleep. This is an attempt to solve the phenomenon of insomnia by generating visual activity, only using the existence of light of the visual activity.

The causes of insomnia or being unable to fall asleep at night are very diverse. The conventional prior art references target all causes of insomnia. The present invention does not deal with all the causes and phenomena of insomnia, as discussed below, and covers only a part of them. Even if it is considered that the conventional prior art references also deal with only the part covered by the present invention, it is clear that the attempts to solve insomnia by generating auditory activity, olfactory activity, and visual activity, as described above, have their own meanings from a brain functional point of view. Nevertheless, it cannot be said that these are successful to solve insomnia.

Therefore, an investigation is required to understand the cause of insomnia more accurately from a brain functional point of view and to solve the cause thereof in a brain functional and fundamental way.

SUMMARY OF THE INVENTION

In the course of our lifetime, the case that we suffer from an acquaintance's death, divorce (or a spouse's unfaithfulness), loss of court proceedings, money problems, unemployment, etc., or that we suffer from changes in environment including a change of a bed, an occupational characteristic, such as triple shift or double, or the nature of work causing stress, thoughts related thereto come into the mind one after another. If such a "flow of thoughts" continues to happen at night, we may not be able to sleep.

The reasons for not being able to sleep at night are diverse and vary from person to person, but in the end, are because "an insomniac cannot cut off or stop the flow of one's thoughts". When this phenomenon happens, the entire brain is in a working state, which is an awake state, so that it is unable to sleep with the general sleeping function. The term "insomnia or the phenomenon of being unable to sleep" in the present invention refers to this phenomenon, and in general, may be referred to as "the insomnia (phenomenon) ". The present invention deals only with this phenomenon.

Accordingly, the "technical problem to be solved" has been made in order to stop or disconnect the thinking(or the flow of thoughts of an individual) when the individual is trying to sleep at night There are some cases in which an emotion such as anxiety and worry, anxiety or fear may be activated in the phenomenon of not being able to sleep, and sometimes, of waking up and being unable to fall asleep again. This is because of the phenomenon of emotion itself being continually projected, which is the same as that of continual thought. This emotional projection phenomenon is included in insomnia or the phenomenon of being unable to sleep in the present invention. The emotions being projected continuously will be discussed in the case that thoughts are continuously generated.

Looking further, cognitive activity is an integrated activity of signal and experience. That is, in the case of visual activity, when a visual signal enters the brain, a corresponding visual experience is projected, and this signal is integrated with experience to be visual activity. Therefore, when we attempt to sleep, we close our eyes and try to sleep. By preventing the influx of visual signals and projecting the visual experience, no activity happens in the brain for sleeping. This is the "general sleeping function or functional ability to sleep."

However, in the case of insomnia, the thinking activity continues, even though the eyes are closed, which means that experience-projecting happens, i.e., the experience-projecting function is malfunctioning in the sense of brain function. The problem to be solved is, in other words, "a malfunction of the experience-projecting function". This malfunction also develops itself, and the flow of experience-projecting becomes more and more intense as time passes.

The inventor reveals that, in the human brain, the "thinking(thought) activity area" and "the ultimate visual activity area" are the same area. This means that thinking and visualization cannot be undertaken at the same time, and that a choice must be made there between. Based on this premise, the present invention provides a means to create visual activity to solve the technical problem, enabling one to push out one's thoughts through visual activity.

This is discussed in further detail below. First, we examine what thought(the thought process) is from the perspective of brain function.

At the top of the frontal lobe, there is a "visual screen (area). The term "visual screen" is the inventor's term, and its traditional term used in the brain function field is "Brodmann's Area 9" (When the Internet are searched, related images can be found).

Thinking is the use of language to build a story on the visual screen (area), which is like drawing a picture on the visual screen. The meaning of "using language" refers to using language as if it were in a speech state by sound experience projecting.

A malfunction of the projecting experience mentioned in the technical problem refers to a malfunction of sound experience projecting.

In addition, the visual screen is an area in which a visual shape is ultimately displayed due to final integration through several visual signal processing processes and several experience projecting processes. In view of the visual image shown here, the subject of recognition will adopt a visual understanding and judgment.

That is, the visual screen is where thinking occurs, and also where the visual image finally appears. Visual and thinking activities may be regarded in the relationship between the first- and second-floor. This means that most of the two activities are in common. However, both thinking and visualization cannot simultaneously occur on the visual screen.

Therefore, when a picture of the thought is being drawn on the visual screen, the visual image of the visualization is displayed on the visual screen, and if maintained for a while, thinking is stopped along with sound experience projecting, resulting in immediate sleep. Here, the stopping of thinking and sleeping is a single phenomenon: To fall asleep after thinking is stopped is one phenomenon, and the phenomenon of sleep is a phenomenon (which occurs) when thinking stops. Falling asleep in this situation immediately can be considered falling asleep due to the laws of nature. This is what the inventor has discovered.

Thus, the present invention causes visual activity to induce the above phenomenon and provides a means and related information for maintaining the visual activity.

In other words, the device for forming a new sleeping function against insomnia for solving the technical problem according to the present invention, comprises a storage unit for storing a plurality of visual images; a voice output unit for outputting voice; a display unit displaying various kinds of information; and a control unit which controls so as to display the initial screen, the instruction manual, the start button, and the toolbar on the display unit according to the user's operation, wherein the initial screen comprises the instruction manual button, the selection window which automatically determines the end time when the apparatus starts to operate, and the START button; the above instruction manual comprises the previous screen button connected to the above initial screen, the home button, and the next screen, the text button moving to each chapter representing the instruction manual which is divided into six chapters, and a region in which the instruction manual appears; the above controller unit displays the visual image including the image selection buttons connected to the initial screen through the above display unit; the audio output unit repeatedly plays a sentence of voice "Open eyes" connected to the above initial screen every 20 seconds from the moment the START button is pressed until the operation of the apparatus is completed; the toolbar comprises a home button, a voice on-off button, a volume button including a volume controller, an illumination button including a lighting controller, and an automatic screen switching button; the above control unit displays a visual image including a 'circle with a dot in the center' as the first screen through the above display unit when the START button is pressed.

The control unit includes a function of causing an image illustrating an angle of the eyeballs when the user is lying sideways to appear on the display unit for 15 seconds every 5 minutes after pressing the START button. The reason for including this function will be described later in the "Description of the preferred embodiments" as follows.

Regarding methods, the methods for forming a new sleeping function against insomnia for solving the technical problem according to the present invention are two. Each thereof comprises a visual image displayed to the user, controlling an angle of eyeballs and a sleep behavior or causing a user to sleep by stopping a flow of thought through learning instruction from an instructor.

The device and methods for forming a new sleeping function against insomnia according to the present invention can solve the phenomenon of insomnia by creating and developing a new sleeping function separately from the general sleeping function.

In more detail, if a means for generating visual activity (every night) is provided, visual activity occurs, and when visual activity occurs, thinking activity is stopped and the technical problem can be solved, by which the effect of sleep is generated. This means falling asleep in "another condition by a new sleeping function", which is different from a general sleeping function.

Furthermore, if fulfilling the new sleeping condition each day, it becomes functional training or functional learning itself, which creates, develops, completes(forms) and provides a new sleeping function. Substantially and ultimately, a user gets to achieve two sleeping functions: One, in general, is the functional ability to sleep by trying to fall asleep with the eyes closed, and the other is the functional ability to fall asleep by stopping thinking through visualization with the eyes opened. The former refers to sleeping after blocking the influx of signals, preventing the experience projecting from being activated and causing the brain to have no effect, while the latter refers to sleeping by actively causing visual activity.

In the latter case, it is not a function to correct a malfunction in experience projecting, but a new functional ability to sleep by avoiding thinking through the stopping of thinking activity in a situation in which malfunctioning occurs in experience projecting. Under the phenomenon of insomnia, it is the ultimate goal and effect of the present invention to avoid the phenomenon of insomnia every night and sleep, and to form and retain such a new(second) functional ability.

In other words, insomnia means that sleeping is not possible with the general sleeping function (ability), so the present invention's ultimate goal and effect is to create and develop a new sleeping function (ability) that is different from the general sleeping function (ability).

If the user acquires this ultimate effect, even if the user does not use the present invention and the thinking activity continues to happen when the user tries to sleep, the user can stop the thinking activity and fall asleep within 2-3 minutes simply by using visual targets within bedroom with the new sleeping function. This becomes a state of sleep that is almost equivalent to normal person's sleeping through the general sleeping function in a general situation. Moreover, there are no side effects from start to finish.

DETAILED DESCRIPTION OF THE PRESENT INVENTION

The main objective of the present invention is to stimulate the visual activity and also to maintain the effective visual activity in order to provide the effects of the invention to the user. We must understand this to understand the composition of the present invention. Hereinafter, with reference to the accompanying diagrams, a preferred embodiment in which the device for forming a new sleeping function against insomnia is carried out on a smartphone.

Figure 1A:
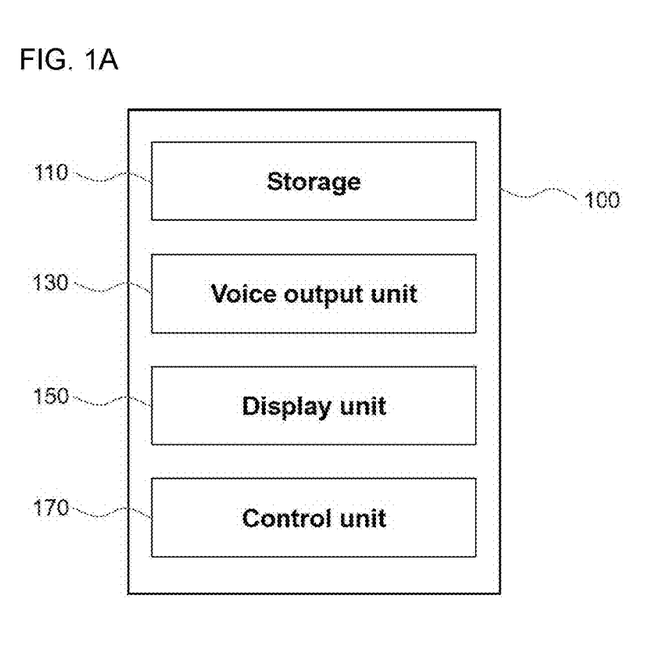
FIG. 1A is a block diagram illustrating a device for forming a new sleeping function against insomnia to a preferred embodiment of the present invention.

FIG. 1a is a block diagram illustrating a device for forming a new sleeping function against insomnia according to a preferred embodiment of the present invention.

Referring to FIG. 1a, the device 100 according to an exemplary embodiment of the present invention may include a storage unit 110 storing a plurality of visual images, a voice output unit 130 for outputting a voice, a display unit 150 for displaying a variety of pieces of information, and a control unit 170 that controls to display information such as an instruction manual, a start button, a toolbar, and the like through the display unit 150 according to an instruction manual.

Then, the device 100 according to an embodiment of the present invention is described in more detail as follows.

Figure 1B:
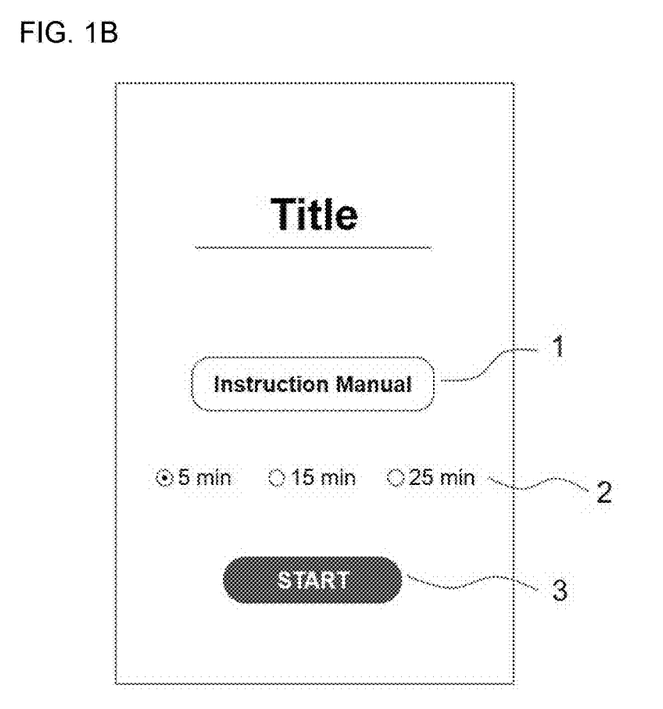
FIG. 1B is a diagram for illustrating the first screen of the invention implemented in a smartphone.
Figure 2:
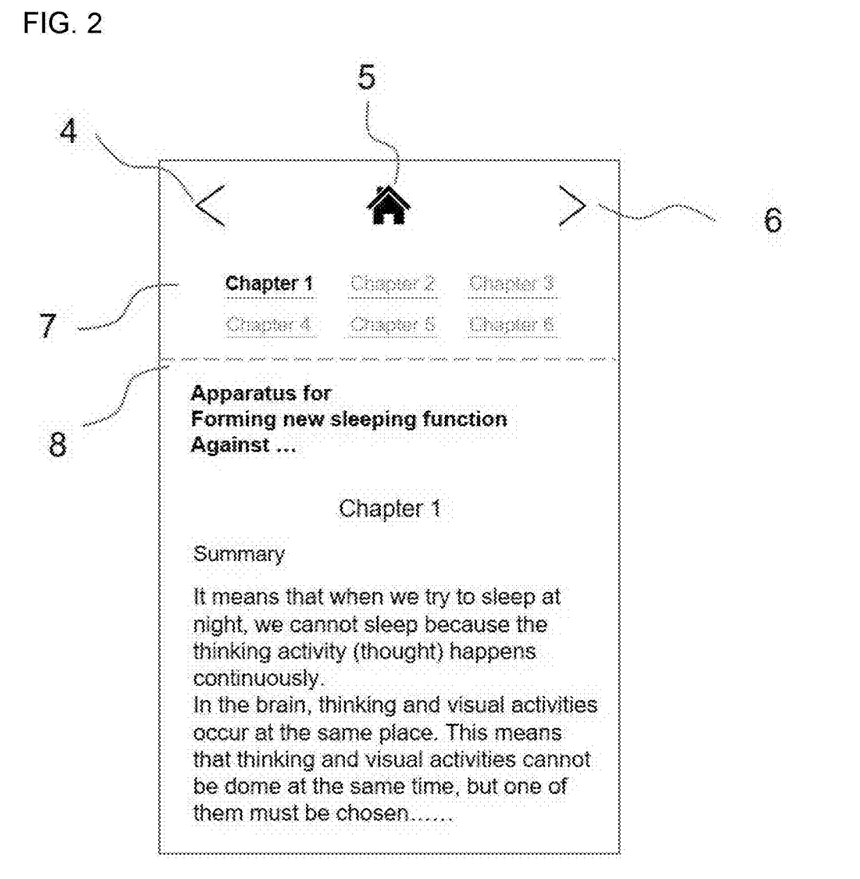
FIG. 2 is a diagram for illustrating the function related to the instruction manual that appears when pressing the instruction manual 1 of FIG. 1B is pressed.
Figure 3:
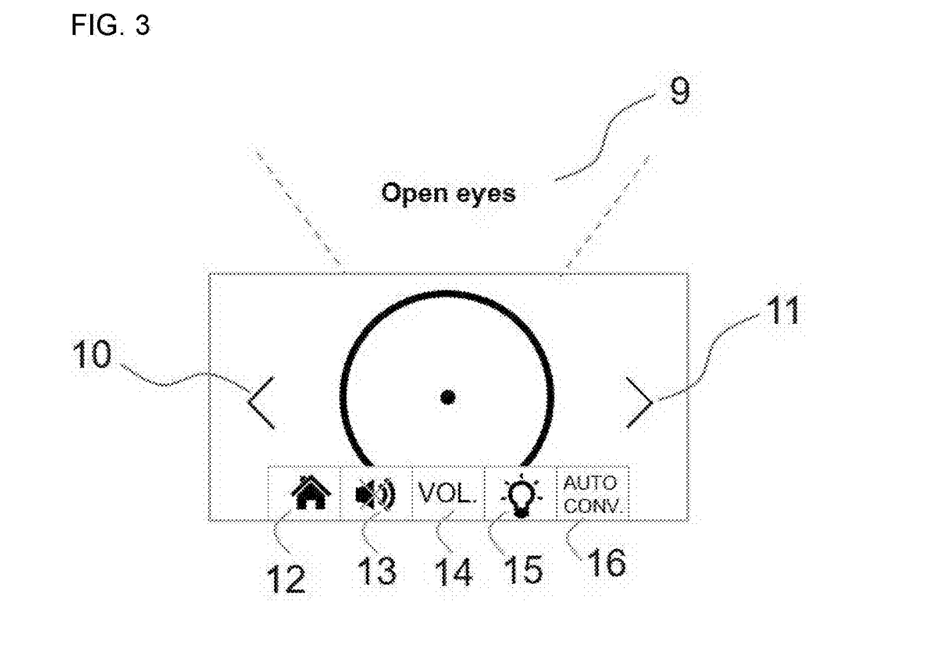
FIG. 3 is a diagram for illustrating the components of the present invention.
Figure 4:
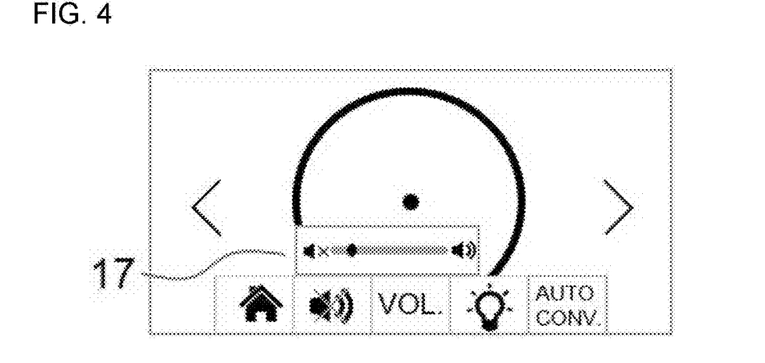
FIG. 4 is a diagram illustrating the pop-up appearance of the volume controller.
Figure 5:
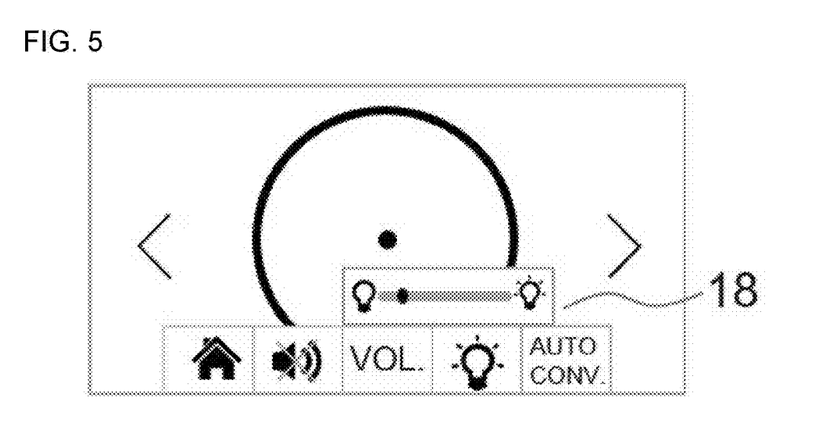
FIG. 5 is a diagram illustrating the pop-up appearance of the lighting controller.
Figure 6:
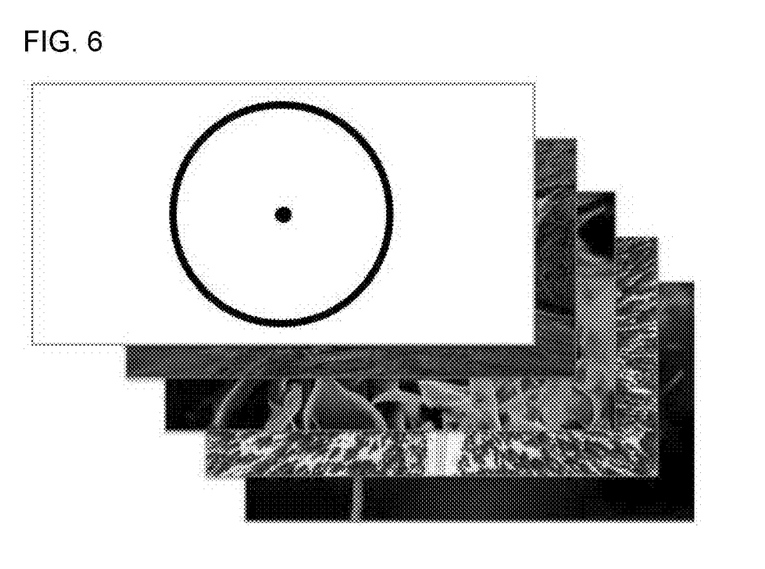
FIG. 6 is a conceptual diagram illustrating a shape in which a plurality of visual images comprising components is prepared.

FIG. 1b is a diagram for illustrating the first screen of the invention implemented in a smartphone, FIG. 2 is a diagram for illustrating the function related to the instruction manual that appears when pressing the instruction manual 1 of FIG. 1b is pressed, FIG. 3 is a diagram for illustrating the components of the present invention, FIG. 4 is a diagram illustrating the pop-up appearance of the volume controller, FIG. 5 is a diagram illustrating the pop-up appearance of the lighting controller, and FIG. 6 is a conceptual diagram illustrating a shape in which a plurality of visual images comprising components are prepared.

FIG. 1b is the initial screen of the device when the present invention is implemented in a smartphone. If the instruction manual 1 is pressed, the instruction manual of the present invention will be opened as an e-book, as shown in FIG. 2. The contents of the instruction manual are almost the same as in this specification. A user who uses the present invention for the first time will be instructed to read the instruction manual.

FIG. 2 includes the previous screen button (4), the home button (5), and the next screen button (5). Reference numeral 7 of FIG. 2 illustrates that the instruction manual is divided into six chapters, and is a character button to move to each chapter. The lower part of 8 (dotted line) of FIG. 2 illustrates a region in which the instruction manual appears. This instruction manual may be in the device as shown in FIG. 2, may be an e-book on a separate homepage, or may be distributed with printed paper. In such a case, the device may be configured without the instruction manual. That is, the configuration of the instruction manual means that the instruction manual is prepared so as to be read before the present invention is used.

Reference numeral 2 of FIG. 1b is the selection window that allows the user to select the automatic stop time after launching the device of the present invention. There are three choices: 5, 15, and 25 minutes. If the user selected 15 minutes and then pressed START 3, the device would automatically stop after operating for 15 minutes. When the device stops after having operated for 15 minutes as selected by the user, if the user still has not fallen asleep, the user can go back to FIG. 1b (home), reselect the operation time, and press START. The three time periods can become the estimated target time that the user chooses "to fall asleep within a certain amount of time". For example, if the user selects 15 minutes, it may signify that the user will sleep within 15 minutes.

Reference numeral 3 of FIG. 1b is the START button, which begins the device's operation when pressed. FIG. 3 is the diagram illustrating the actual starting moment of the present invention. Let us look at this from several perspectives.

FIG. 3 illustrates "a circle with a dot in the center" within the display. First, to induce and maintain visual activity, a visual target must be visible. FIG. 6 illustrates an example of the saved visual image as a visual target, while the definition of a visual image as the visual target in the present invention means two-dimensional(2D) and three-dimensional(3D) images, such as figures, patterns, pictures, photographs, etc. However, except for the 'circle with a dot in the center', other images do not have any special designations. Normally, the user usually will choose one of the images for the night. The visual image in the present invention refers to a still state or a "still cut" such as a single photograph.

4 to 6 images are sufficient as a total number of visual images, but the device will consist of about 10 images. Herein, 4 to 6 images are sufficient, so even if the number of images is more than 8, 10, or even 20, there is no meaningful difference. Comprising a visual image in this specification means storing the visual image of several sheets (10 images) including a circle shape with a dot in the center, and enabling the screen to be switched (screen selection) with the previous screen button 10 and the next screen button 11 of FIG. 3.

Once the user presses the START button 3 in FIG. 1b, by default, the circle with a dot in the center appears, and afterwards, the user can choose the screen with two buttons 10 and 11. However, the visual image only appears fixed in landscape mode, as shown in FIG. 3. Therefore, for example, even if the smartphone is rotated 90 degrees from FIG. 3 to FIG. 1b, the visual image stays fixed, and will not change its orientation.

FIG. 3 describes the response when the user presses the START button 3, which begins with the voice saying, "Open eyes" 9. In the audio output section, the voice repeats the command "Open eyes" 9 every 20 seconds from the moment the START button is pressed until the device finishes the operation. To induce visual activity, the user has to open his or her eyes, but in actual use, his or her eyes will almost close themselves automatically, so this is why the sentence is repeated to keep them open. This will be explained further later. Herein, "every 20 seconds" means to repeat the replay frequently in such amount of time interval. Thus, an interval of 15 to 25 seconds, i.e. every 15 seconds, every 18 seconds, every 22 seconds or every 25 seconds will be same. This means that "every 20 seconds" would be the most desirable for the time interval, since it is inevitable to select the time interval when programming.

FIG. 5 illustrates also a toolbar. The toolbar 12, 13, 14, 15 and 16 is configured so that it appears on the screen when pushed up with the finger, and disappears outside the screen when pushed down with the finger. FIG. 3 illustrates a state in which a toolbar is displayed on the screen. 12 of FIG. 3 is a home button, 13 is a voice on-off button, and 14 is a volume button. When the volume button 14 is pressed, the volume controller 17 pops up as shown in FIG. 4. In order to remove this pop-up window after the volume control is completed, the volume button 14 is pressed again. 15 of FIG. 3 is an illumination button. When this button is pressed, the lighting controller 17 pops up as shown in FIG. 5. After adjusting the illumination, the illumination button 15 is pressed again to remove the pop-up window 18. It is important to adjust the degree of illumination, because the user watches these visual images in a dark place rather than in a bright place. 16 of FIG. 3 is a screen automatic switching button. When pressing this button, the 10 visual images are configured so as to be switched continuously and automatically at an interval of about 10 seconds.

The explanation illustrates the means (device) implemented in a smartphone, which can be implemented on a tablet PC in such a way. Since a smartphone or a tablet PC is relatively expensive, only the above described configuration can be reproduced on a separate, independent device so as to be used at a relatively low price.

Method of Using the Device and Discussion thereof

What does the user do? The two functions, i.e. thinking activity with the eyes closed and visual activity with the eyes open are constantly in a tug-of-war or a fight for control.

If the user sees an image from the present invention when trying to sleep at night, his/her eyes will soon close, and thoughts will arise. When the user looks at the image again with eyes open, his/her eyes will close again and thoughts will again return. Then the activity of looking at the image again with the eyes open will be repeated. Briefly, the user continues to fight a tug-of-war between closing and opening eyes or, thinking and seeing.

Twenty years ago, when the inventor realized that he could not sleep because of his persistent thoughts, the inventor developed the hypothesis that since the thinking activity and the visual activity occur at the same place, the visual activity can suppress the occurrence of the thinking activity. It was then, for the first time, that inventor was able to fall asleep within around an hour after inducing visual activity. This day is still very much alive in the memory of the inventor. Once inventor closed his eyes, it was very comfortable to keep them closed.

Looking back on this, the inventor remembers that it was very difficult to open his eyes and how irritated he was. Also, the inventor found out that the flow of thinking activity was very strong. Since it is difficult to open one's eyes independently within this strong flow, the inventor thought that it might be easier if someone would tell him, "Open eyes". The reason why the present invention keeps saying "Open eyes" is because it is difficult for one to open one's eyes independently, and this is why it is one of the main components of the present invention. For this reason, it is critical to not turn off this voice, even when it is irritating. Though it may seem irritating at times, the intensity of one's irritation will decrease as time goes on. The volume on/off button 8 in FIG. 5 is provided so that the voice can be turned off in special situations when it is inconvenient to have the voice talk, such as when one is sleeping amongst many people, and it isn't meant to be used to turn off the voice just because it is irritating.

Once the eyes close, 5-15 minutes of time passes by quickly. At this point, the user will realize the significance of the support provided by the voice.

From this moment, as long as the user is closing his/her eyes, he/she must realize that the thinking activity will not be stopped, resulting in no sleep. Therefore, the user must keep his/her eyes open, and induce visual activity by looking at the image. The user must also realize that the final victor in the tug of war or battle between the two functions will always be the visual activity. Every day, and always, the visual activity will win, allowing one to sleep.

Visual activity. (a) The visual activity consists of two methods, one of which works with various parts of the brain integrated into one system to cause activity, while the other causes partial activity. These two activities do not become active by conscious selection, but rather are selected unconsciously as the visual activity occurs. The former is the visual activity that stops the thinking activity to allow sleeping. Let's call the former activity, in which the visual activity occurs, "taking-photo". When "taking-photo" takes place, thinking activity is stopped and sleeping occurs, due to the law of nature. For reference, if we are to watch a movie, most of the time is spent by the latter.

Figure 7A:
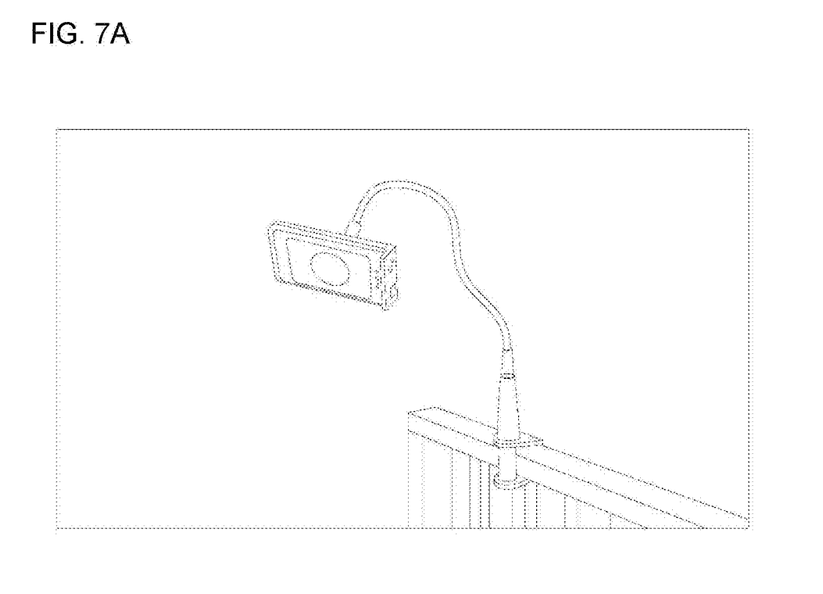
FIG. 7A is a diagram illustrating a holder holding a smartphone.
Figure 7B:
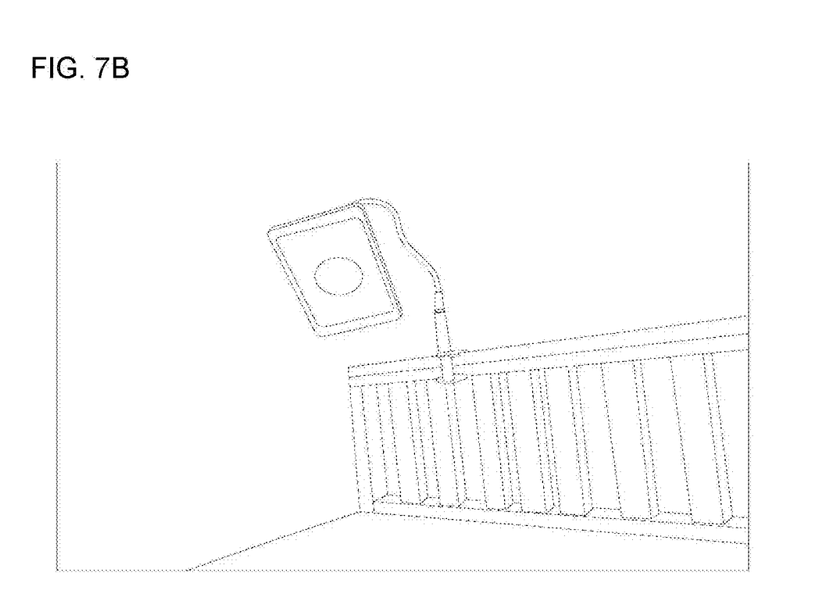
FIG. 7B is a diagram illustrating a holder holding a tablet PC.

(b) For actual use, see the holder shown in FIG. 7a and FIG. 7b. This holder can hold either a smartphone or a tablet PC.

(c) When viewing visual targets(visual images) to cause visual activity, it is generally difficult to escape from the flow of thought from the aspect of general behavior(angle or direction of eyeball) when viewing videos or images. For this reason, turn the eyeballs slightly upward (in that angle) when viewing the visual target.

Figure 8A:
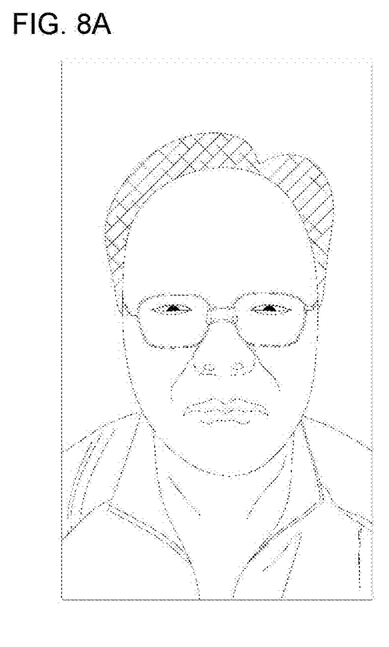
FIG. 8A and FIG. 8b are diagrams illustrating behaviors when performing a general visual activity.
Figure 8B:
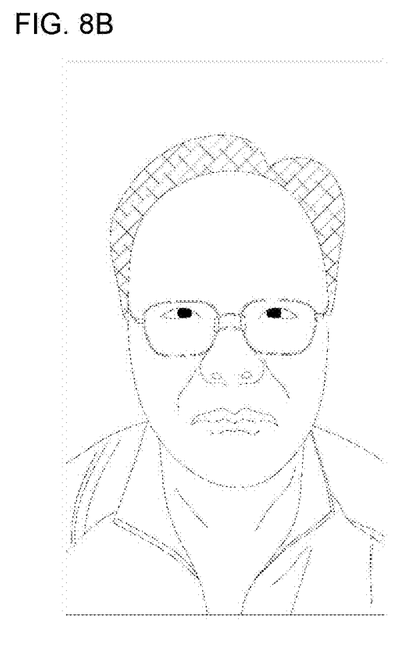

FIG. 8a is illustrating the behavior of looking slightly downward during a normal visual activity, and FIG. 8b is illustrating the behavior of looking horizontally. These kinds of behaviors are to be avoided.

Figure 9:
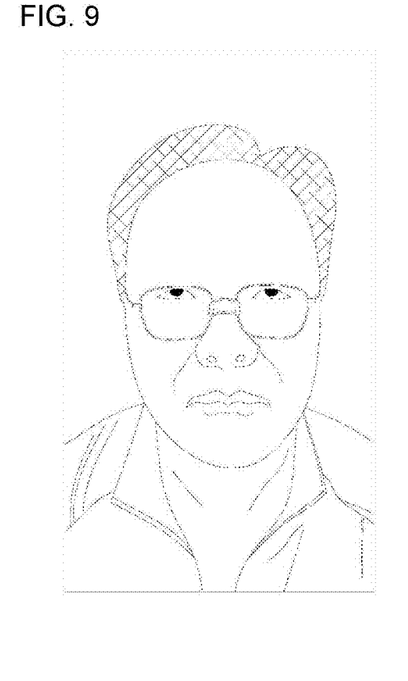
FIG. 9 is a diagram illustrating angles and behaviors of the eyeballs for the visual activity that a user should perform in the future.

FIG. 9 demonstrates the behavior of only moving the eyes a bit upward to view horizontally while keeping one's chin fixed. From now on, the user is expected to cause visual activity through this kind of behavior. For those with glasses, the eyes should be directed just a bit above the top of the glasses. The purpose of causing visual activity by moving the eyes slightly upward like this is to weaken or avoid the (powerful) flow of thinking activity.

Figure 10:
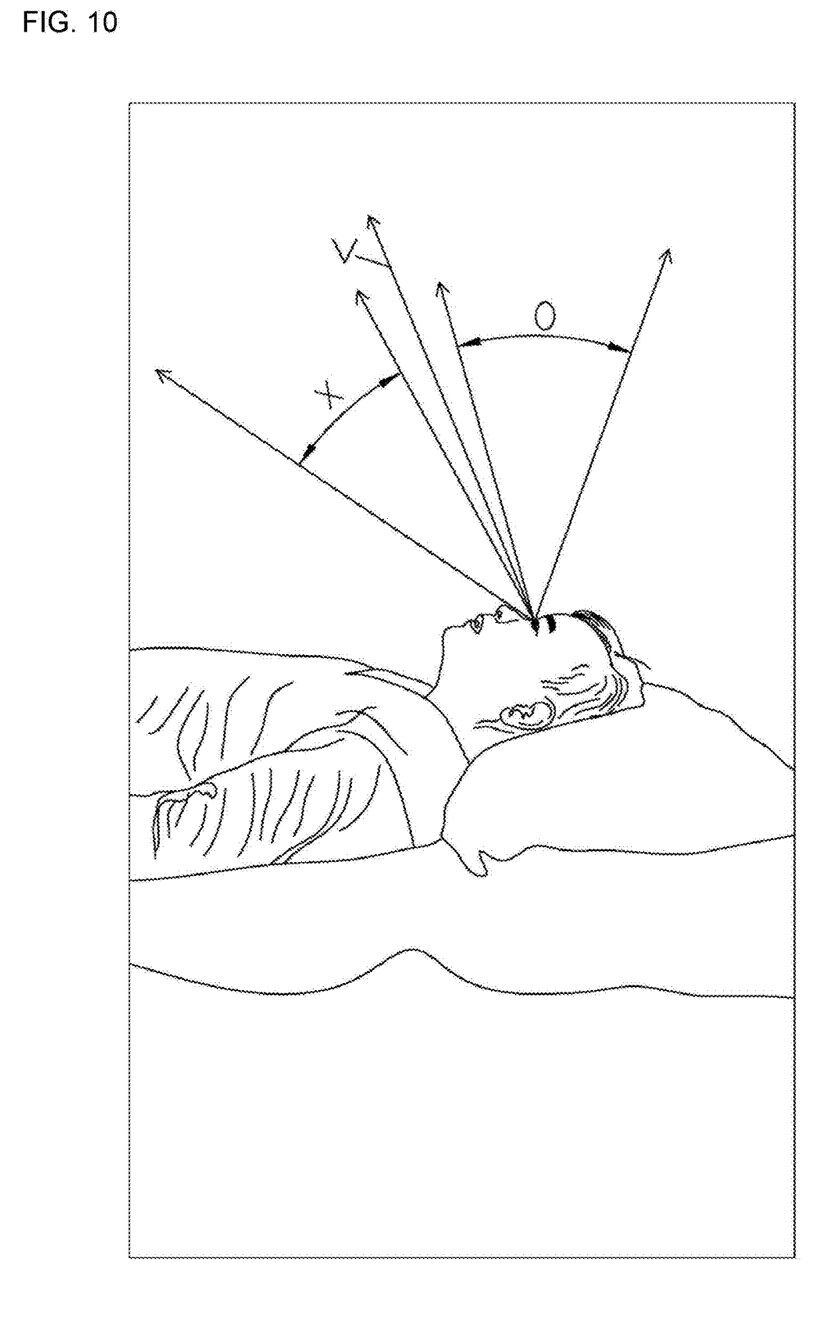
FIG. 10 is a diagram illustrating the range (symbol O) when only the eyeballs are slightly turned up when lying in bed.
Figure 11:
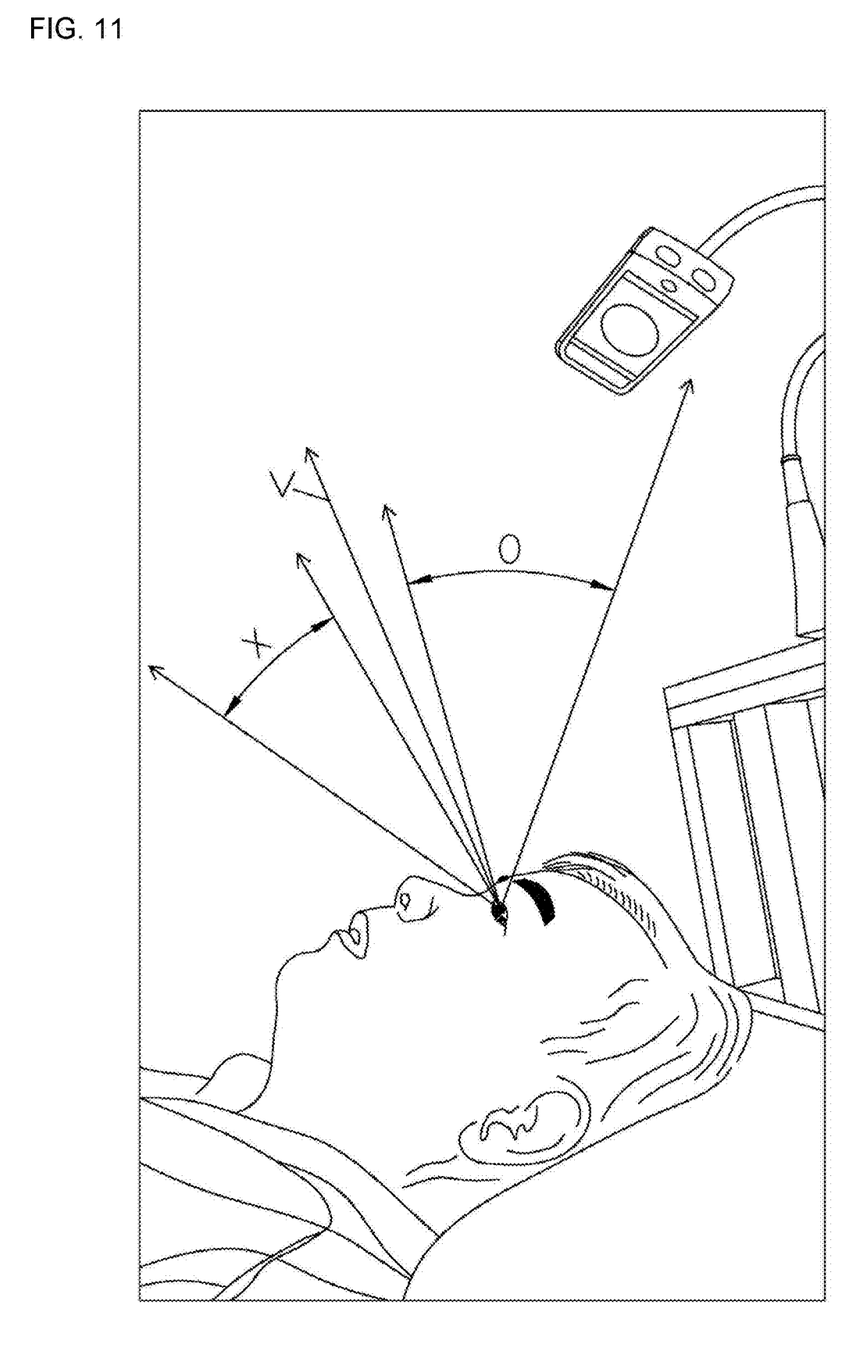
FIG. 11 is a diagram illustrating the angles of the eyeball when the visual image is placed within the range of symbol O of FIG. 10.

FIG. 10 illustrates the virtual vertical line right above the eyes or the virtual horizontal line right in front of the eyes (symbol V: Symbol V in the diagram below represents the virtual vertical or horizontal line to which the eyes are headed towards) when lying on a bed, and the range (symbol O) when only the eyes are shifted a bit upward with the chin fixed. To explain this range in more detail, it represents the range that is a bit higher than the range that is the same or similar to the above V direction. Visual activity is started with the visual image placed within the range of symbol O. FIG. 11 illustrates the situation in which the visual image is placed within the range of symbol O of FIG. 10 and the angle of the eyes. Of course, the "within the range of symbol O" means the range that is natural even when the user moves the eyes a bit upward, and a range that isn't awkward due to raising the eyes to extreme levels. There isn't a numerical value for the physical "degrees". However, the visual target must be apparently above the virtual vertical line or the horizontal line symbol V in FIG. 10.

The above does not present any special difficulties. Unlike the behavior of normal visual activity, the user only needs to think about turning his or her eyeballs upward a little. Later, with experience, any visual behavior and its activity will do, but during the initial process, "taking-photo" can either occur very late or not at all with the eyes' angle of the normal visual activity in FIG. 8. On the other hand, if the user thinks that he or she cannot fall asleep despite a lot of visual activity, it is probably because he or she is doing visual activity in the manner shown in FIG. 8a or 8b. Quickly, the user should turn his or her eyeballs upward and reposition his or her own face or torso.

There is an interesting story to tell the user about this: Avoiding common behavior and raising our eyes a little "upward" is not something the user can understand but something the user has to realize. Actually, the inventor realized that in 99 days out of 100, 15 minutes to 25 minutes are always spent looking at the visual target(visual image) in normal behavior, until the inventor realized that he wasn't falling asleep and immediately raised the eyes to look at the visual image. Usually, it means that the user is wasting from 15 to 25 minutes or more of time every night.

Therefore, in the present invention, if the image illustrating the angle of the eyeballs when the user is lying sideways (for example, FIG. 12 to be described later) appears on the display part for 15 seconds every 5 minutes after pressing the START button 3 on the device and the instruction manual instructs that the meaning of the indication is a signal to check whether the angle of the eyeballs is correct or not, this instruction can prevent the user from losing 15 to 25 minutes every day.

Figure 12:
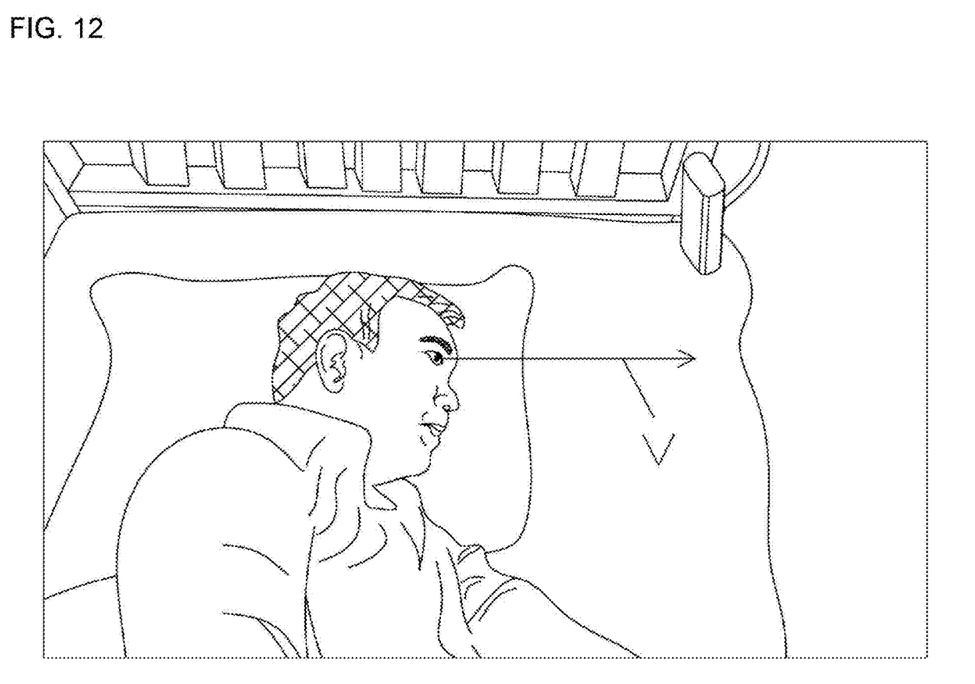
FIG. 12 is a diagram illustrating the right angle of the eyeballs when lying sideways.

(d) FIG. 12 illustrates the proper angle of the eyes when lying on one's side. The visual image is on the horizontal line. It may be easier to fall asleep when lying on one's side compared to lying on one's back. This is because it is behaviorally more natural and easier to raise the angle of one's eyes upward when lying on one's side. Therefore, if the user feels that he or she will not be able to sleep lying on his or her back, think about the angle of his or her eyes and conduct visual activity while lying on one's side.

Users who wear glasses should take them off, and after adjusting the distance so that the visual image is fully visible to the naked eye, confirm the location of the visual image or smartphone in terms of its angle.

Figure 13A:
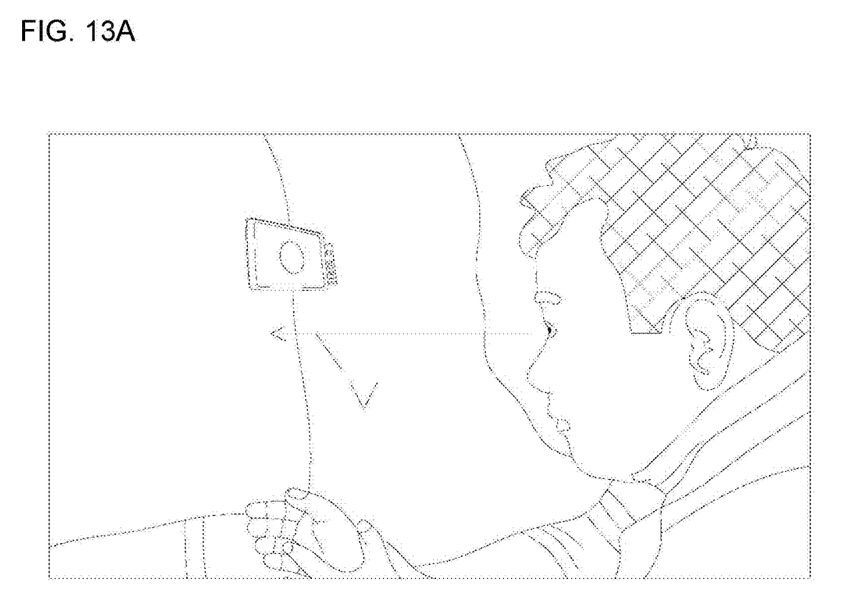
FIG. 13A is a diagram illustrating how to use a smartphone when no holder is present.
Figure 13B:
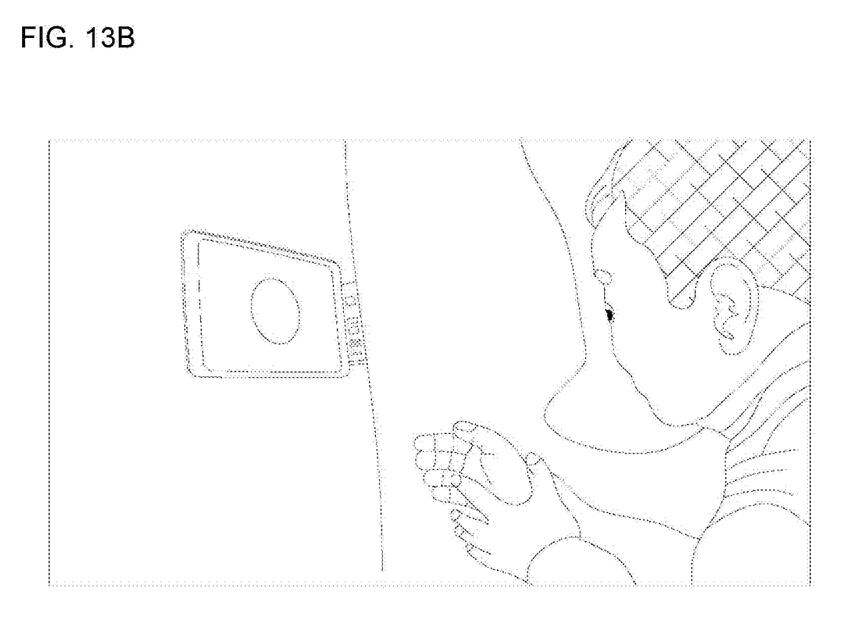
FIG. 13B is a diagram illustrating how to use a tablet PC when no holder is present.

(e) With nothing to hold one's phone or tablet, one cannot engage in the visual activity while lying down, and must be on one's side. FIG. 13a and FIG. 13b show how a smartphone FIG. 13a and tablet PC FIG. 13b can be used with no holders. Use them while leaning them against a wall or a cushion.

(f) The optimum solution is to buy two holders, and use one for lying on one's back and the other for lying on one's side.

Image usage guidance. There are 10 images stored in the device of the present invention. The first image is the 'circle with a dot in the center'. Initially, the user is recommended to use only this figure. Maintain the behavior of continuously looking at the center dot for the majority of the initial process. In other words, maintain this while continuing to look at the center dot. Here, the initial process means a situation in which the flow of thinking activity is strong and the new sleeping function does not exist or is insignificant.

If it is observed that the user is falling asleep within 15-25 minutes while only using the circle, since it is difficult to reach the ultimate goal with only the circle, choose a different image (train with a variety of images). It is recommended to select the image that is after the circle. For a period of time, try "taking-photo" by selecting the second image. If it is observed that the user is falling asleep within 15-25 minutes with the second image as well, select the third image, and so on. In other words, it is good to train using multiple images to achieve the ultimate goal.

However, if the user slept well because "taking-photo" went well the night before, then it is good to do it the same way the next day.

When looking at each image, visual activity is caused by either analyzing or judging while conveniently looking at the whole image in a single vision, or delicately analyzing and judging a part of the image. The thinking activity of the present invention includes both the analysis and judgment activities. Analysis and judgment encompass the act of observing various things, such as color, shape, sense of distance, sense of mass, and counting.

If only the direction of the eyes is directed to the visual image, "taking-photo" may not occur. One must analyze and judge. It is observed that "taking-photo" occurs approximately 30% of times for those analyzing and judging the whole image, and approximately 70% for those analyzing and judging partially.

On those special days when the user thinks it is strangely difficult to fall asleep, when the user presses button 16 (automatic screen transition) in FIG. 3, ten prepared visual images transition with 10 seconds given for each, so try to conduct visual activity by partially analyzing and judging again, after analyzing and judging each image as a whole in a calm mood.

Waking up while sleeping. There are times when the user may wake up, due to a phone call, anxiousness, or worry, while sleeping at night. At this time, the user may be pressured to fall asleep again quickly, or worry while thinking "it is going to be terrible if I don't fall asleep until morning". It is important to get rid of these thoughts, taking confidence in the wisdom of thinking, "I'll be able to sleep again soon using visual activity," and keeping his or her mind comfortable or peaceful. One must look at the visual image with this type of comfortable mindset.

Also, after waking up after sleeping, the user's body still feels sleepy, so the user must get rid of that sleepiness completely to be able to sleep again. The user must realize that the user cannot transition him or her to the status of sleep when the user feels sleepy, but when the user gets rid of that sleepiness and have a clear consciousness. In the range of general sleeping function, sleepiness can signify the connection to sleep, but since the user isn't able to sleep with the general sleeping function now, it signifies that the user isn't able to sleep while the user feels sleepy.

If the user woke up around 2 in the morning and is feeling sleepy, instead of being hasty and hurrying up to directly connect that sleepiness to sleep, maintain a peaceful mind until the sleepiness is gone, and once it is gone (which can take around 30 minutes to two hours), prepare the visual image again and try to sleep again through visual activity.

Looking deeper into the relationship with sleepiness, while trying out visual activity for the first time using the app(the invention), the user might think it strange to experience this clearing of consciousness and the disappearance of sleepiness, but the user must realize that sleep comes with a lack of sleepiness and a clearing of consciousness.

Functional learning. To create and grow this new sleeping function is to develop a functional learning process. This is like the functional learning of learning to drive a car. By growing each new sleeping function each day, the user accumulates daily experience.

Experience accumulates over time, and with it, the time one requires to lie down and fall asleep decreases, bit by bit. For some who weren't able to sleep at night and could only sleep 1-2 hours in the morning for a long time(for example, a decade or two decades or three decades), they may fall asleep with the help of the present invention, but then wake up again within an hour. It is important to note that in this case, waking up again is a separate problem, and the fact that the user slept for at least an hour is important. This less than an hour of sleep will continue to evolve quantitatively and qualitatively with the accumulation of experience.

Even if the user falls asleep and wake up and the user cannot go back to sleep, the user will eventually sleep without waking up until the morning, as the user develops this skill further each time the user wake up. Once the user has the time and space to spare as the user accumulates experience, the user will know whether or not the user has carried out the "taking-photo" process. Therefore, the user will know that "taking-photo was conducted and that the user will soon fall asleep. After "taking-photo", the user will sleep after exactly 5-6 seconds.

Ultimately, the user will be able to fall asleep within 2-3 minutes using any visual target (anything that can be seen is a visual target) in the room, without the present invention. That is, unlike the general sleeping function, a separate new sleeping function is formed and retained. Actually, the user will be able to sleep using each of the two functions. At first, one might try to sleep with the general function of closing one's eyes, but after realizing that one is not able to sleep due to thoughts that are occurring, one will be able to open one's eyes and sleep by conducting visual activity.

The time required for achieving the ultimate learning goal. Let's assume the case of those who could not have fallen asleep at night for a long time, for example, could not sleep all night and only sleep for an hour or two in the morning for a period of 10, 20, or 30 years. It can be deduced that the time required to complete the new function to the extent is between 6-9 months to 33 months. This deduction is based on the process which the inventor has gone through to escape from the phenomenon of not being able to sleep, and the language development process of the baby, and the development process of the brain function.

The above description illustrates that the present invention is realized by a so-called application. This is for self-learning. This makes it impossible or difficult for illiterate people or elderly people to use the present invention by themselves. Otherwise, in functional training or learning, the term "self-learning" means a high possibility of trial and error.

The present invention may be realized in the form of a distance learning method and an instructor-led offline learning method. The two methods will be discussed as follows.

Distance Learning Method

Recently, videotelephony allows people to talk with each other while looking at images of each other using smartphones or web cameras via the Internet. In addition, current distance learning devices allow learners and instructors to look at images of each other. In general, instructions are performed by displaying visual images (e.g. pictures or diagrams) as well as images of test papers instead of the instructor. That is, a user may be provided with an instruction while looking at the face of the instructor or be provided with the visual images (e.g. pictures or diagram), by using smartphones.

As the user and the instructor use such distance learning devices, the face of the user, captured by the camera of the smartphone of the user, may be displayed on the monitor of the instructor, so that the instructor may instruct to adjust (control) the angles of the eyeballs and the sleep behavior of the user while looking at the monitor. The instructor may demonstrate the sleep behavior to the user.

An instructor may provide an online instruction to the user in a situation in which the user is connected to the instructor using the distance learning device while generally staying at home (without having to visit any place). The instructor may help the user sleep by cutting of the flow of thoughts or by adjusting the user's brain function to form a new sleeping function by adjusting the angles of the eyeballs and the sleep behavior of the user or training the user regarding the angles of the eyeballs and the sleep behavior by providing and instructing the user to look at one of visual images, including "circle with a dot in the center". Here, the adjustment of the sleep behavior which involves ordering the user to open eyes when the user close them and the training refer to the instruction of the instructor provided regarding those described above in the instruction manual according to the situation. This is the "distance learning method." The distance learning method is typically performed when the user attempts to sleep in bed.

Even in the case in which the user is illiterate, the distance learning allows the user to obtain the effect of the present invention by voices and demonstration of the instructor. When the user is literate, the distance learning may significantly reduce trials and errors compared to the self-learning of the present invention, so that the user may more effectively and efficiently learn to form the new sleeping function.

Offline Learning Method

An instructor may provide an offline instruction to a learner having insomnia by visiting the learner or inviting the learner to an instructor's clinic. The instructor may help the learner (user) sleep by cutting the flow of thoughts or by adjusting the learner's brain function to form a new sleeping function by adjusting the angles of the eyeballs and the sleep behavior of the learner or training the learner regarding the angles of the eyeballs and the sleep behavior by displaying visual images to the learner. Here, the adjustment of the sleep behavior, the training, and the adjustment of the brain function refer to the instruction of the instructor provided regarding those described above in the instruction manual according to the situation.

The instructor may demonstrate the sleep behavior to the learner. Regarding the display of visual images, the learner may achieve the learning in the process of using the self-learning application or the instructor may provide the learning to the learner by attaching prepared visual image(s), such as "circle with a dot in the center," to the wall above the bed headboard or on the ceiling. This is the "offline learning."

It is understood that the offline learning may be provided by a single instructor to one or two persons(learners). However, the offline learning has more significant and better results compared to the learning using the self-learning application and the distance learning method.

It is understood that the offline method can be implemented even in an environment without electricity, without a smartphone, and without the Internet, and that, essentially, the application for self-learning and the distance learning method are to expand the range of use of the offline method by using contemporary technology.

In brief, the present invention may be embodied and provided in the form of (i) a self-learning application, (ii) distance learning, and (iii) offline learning. All of these forms have an essential idea of "adjusting the brain function of the learner(user)." The adjustment of the brain function means to help the learner to sleep by disconnecting the flow of thoughts, which is a major reason of insomnia, or to form a new sleeping function in the brain. Such adjustment of the brain function is performed by adjusting the sleep behavior or learning instruction.

Important point in this case is that the above-mentioned three types are in the complementary relationship. For example, a user may undertake self-learning by using the application after the distance learning for one week, because the cost of the distance learning is expensive. Here, if the self-learning is performed using the relatively-inexpensive application after the period of the distance learning is set to be as short as possible, unnecessary costs can be prevented.

Overall Discussions

In summary, the inventor has studied the brain function through second language acquisition (foreign language acquisition) with a focus on listening to the second language sound (English sound) from TV or radio in Korea. In addition, the inventor recruited learners and taught foreign language acquisition (acquisition of English).

It is widely known that adults have a difficult time acquiring a second language. This is because, when the second language is heard for its acquisition, instead of the second language sound causing a reactivity that supports the development of the second language function, it is judged based on the thinking activity of the first language function. Therefore, most of the second language sound that is heard goes to waste, without any meaning. As such, it is necessary to either stop or limit the thinking activity of the first language function, so within the classroom, this thinking activity is either limited or suppressed through two methods.

The first thing a learner does when he/she comes to the classroom is to look at the circle (diameter of around 1-1.2 meters) with a dot in the center for around 15-25 minutes, and then, when listening to English (second language sound) through earphones or loud speakers, he/she slightly turns his/her eyes upward to look at the dot on the ceiling. The two practices are done to either suppress or limit the thinking activity.

Looking at the circle calms the nerves and gradually weakens the thinking activity(frontal lobe activity). The reason why this occurs is unknown, but when the eyes are turned a bit upward to look, the thinking activity is limited and suppressed. This is because the direction of the vision is placed on the edge of the area where the visual activity or thinking activity takes place. Since the thinking and visual activities occur in the same area, it means that the thinking activity occurs at the outskirts of the thinking activity area, and at this time (according to the laws of nature) the thinking activity becomes weaker, or more restricted.

The inventor deploys two means in this instruction manual(specification) that are used to weaken or limit the thinking activity that have always been used by learners in the inventor's classroom. In this sense, the inventor intends to represent to end the argument on insomnia further, in other words, to eliminate insomnia in this world with this invention.

20 years ago, the inventor was dealing with sleep problems. By focusing on the continuously occurring thinking activity as the cause, the inventor achieved sleep by suppressing this activity through continuous visual activity. He himself escaped from insomnia after about one year struggling. As a person who studies brain functions, the inventor has continuously been observing what was going on in his head.

Even after that, there were times the inventor was unable to sleep or would wake up while sleeping, but at each time, he was observing how the visual activity helped to sleep. One day, the inventor couldn't sleep due to thoughts, so he realized, "It is because of my thoughts that I can't sleep!" and the inventor observed that he could fall asleep by opening his eyes, allowing them to wander in search of a visual target, and conducting a visual activity using the visual target. At that time, this act lacked any conscious (intentional) behaviors, and simply occurred automatically. This was novel.

So the inventor self-observed his sleep behavior for some time:

The act of trying to sleep with eyes closed using the general sleeping function was observed. After deciding while trying to sleep in a conventional manner that the inventor wasn't going to be able to sleep due to his thoughts, as was described above, he found that by engaging in the act of opening the eyes immediately, looking around for a visual target and conducting visual activity for a couple of minutes, he was able to achieve sleep. It was observed that the initial flow of the thought was weakened(decreased) by about $1/20$ at the time of observation.

The observation illustrates that the general sleeping function does not work under insomnia, and that sleeping is not possible even if the flow of thought is weak until it is suppressed. In addition, it illustrates that there is another (new) sleeping function by causing visual activity, which is completely different from the general sleeping function. It illustrates that, even under the phenomenon of insomnia, if this new sleeping function is completed and formed, anyone can sleep as if normal person sleeps by the general sleeping function under the general circumstances.

It should also be understood that the intensity of the flow of thought is different for each person. When dealing with the phenomenon of insomnia, it should be understood that even if the basic principles discussed are the same, the specific details may differ depending on the intensity of the flow when dealing with each concrete result. It is therefore necessary to understand that it is not possible to uniformly presuppose or deal with all people.

It will be helpful if the learners who are using the present invention for the first time would remember the intensity of the first day's thought, use it as a reference, and observe the change of the intensity at each moment until the next ultimate goal is reached.

It reveals that the new sleeping function is formed and functions as a second sleeping function, or that its existence is possible according to the training/learning, which is important since they signify the advent of "direction" within the discussion of the phenomenon of not being able to sleep, or, insomnia.

Before revealing the existence of a new sleeping function, the inventor was only trying to write one or two pages about "the phenomenon in which the constant thoughts cause insomnia" when writing a book on brain function, but since the finding of the new sleeping function, he decided that this phenomenon had to be dealt with separately, which led to the creation of this writing and the present invention.

As mentioned, the prior arts using the auditory activity or the olfactory activity are those with the eyes being closed, which have the premise opposite to the present invention and cannot expect or predict the goal and effect of the present invention. In other words, the prior arts are different from the present invention in terms of composition, goal and effect. Herein, the meaning of "the premise opposite to the present invention" is as follows: Continued occurrence of thoughts and their flow becoming stronger as time passes (the passage of time, in a broader perspective) are caused by closing eyes. However, without understanding this causal relationship, they are trying to sleep within the general category of sleeping function with closing their eyes. They must understand the causal relationship, and realize that there is a new sleeping function with opening their eyes to positively generate the visual activity, which is quite different from the former.

Although the preferred embodiments of the present invention have been described in detail, the present invention is not limited to the specific preferred embodiments described above without departing from the key points of the present invention claimed in the following claims. Anyone who has ordinary skill in the art to which the present invention pertains may perform various modifications and removals, replacements, additions, and bypasses of some components, and the like, but they will fall within the scope of the claims.

What is claimed is:

1. A device for forming a sleeping function against insomnia, the device comprising:

a storage unit;

a voice output unit for outputting voice;

a display unit for displaying a variety of information; and a control unit for controlling a variety of information on the display unit, wherein the storage unit stores a plurality of visual images, the control unit controls displaying an initial screen, an instruction manual, a start button, and a tool bar on the display unit according to a user's manipulation, the initial screen has an instruction manual button, a selection window for determining a time when the device starts automatically and ends automatically, and the start button, the instruction manual includes a previous screen button connected to the initial screen, a home screen button, a next screen button, a text button indicative of the instruction manual which is divided into six chapters, and a region in which the instruction manual appears (under an 8-dot line) for moving to each chapter, the controller unit displays the visual images, through the display unit, including a visual image selection button connected with the initial screen, the voice output unit repeatedly plays a vocal recording "Open eyes" at intervals of 20 seconds until an operation of the device stops once the start button is pressed, the toolbar includes a home button, a voice on-off button, a volume button including a volume controller, an illumination button including a lighting controller, and an automatic screen switching button, the control unit displays the visual image including a circle with a dot in the center in a first screen on the display unit when the start button is pressed, and the control unit displays on the display unit an image showing an angle of eyeballs of the user when the user is lying sideways, for 15 seconds at intervals of five minutes, after the start button is pressed.

* * * * *